(12) United States Patent
Reschke (10) Patent No.: US 7,241,294 B2
(45) Date of Patent: Jul. 10, 2007

(54) PISTOL GRIP ELECTROSURGICAL PENCIL WITH MANUAL ASPIRATOR/IRRIGATOR AND METHODS OF USING THE SAME

(75) Inventor: Arlan James Reschke, Boulder, CO (US)

(73) Assignee: Sherwood Services AG, Schaffhausen (CH)

(*) Notice: Subject to any disclaimer, the term of this patent is extended or adjusted under 35 U.S.C. 154(b) by 448 days.

(21) Appl. No.: 10/716,776

(22) Filed: Nov. 19, 2003

(65) Prior Publication Data
US 2005/0107782 A1 May 19, 2005

(51) Int. Cl.
*A61B 18/14* (2006.01)
(52) U.S. Cl. .......................................... 606/41
(58) Field of Classification Search ............... 606/41
See application file for complete search history.

(56) References Cited

U.S. PATENT DOCUMENTS

| | | | | |
|---|---|---|---|---|
| 2,102,270 | A | * | 12/1937 | Hyams ................ 606/49 |
| 2,993,178 | A | | 7/1961 | Burger |
| 3,058,470 | A | | 10/1962 | Seeliger et al. |
| 3,219,029 | A | | 11/1965 | Richards et al. |
| 3,460,539 | A | | 8/1969 | Anhalt, Sr. |
| 3,494,363 | A | * | 2/1970 | Jackson ................ 606/42 |
| 3,648,001 | A | | 3/1972 | Anderson et al. |
| 3,675,655 | A | | 7/1972 | Sittner |
| 3,699,967 | A | | 10/1972 | Anderson |
| 3,720,896 | A | | 3/1973 | Beierlein |
| 3,801,766 | A | | 4/1974 | Morrison, Jr. |
| 3,801,800 | A | | 4/1974 | Newton |
| 3,825,004 | A | | 7/1974 | Durden, III |
| 3,828,780 | A | | 8/1974 | Morrison, Jr. |
| 3,875,945 | A | | 4/1975 | Friedman |
| 3,902,494 | A | | 9/1975 | Haberlen et al. |
| 3,906,955 | A | | 9/1975 | Roberts |
| 3,967,084 | A | | 6/1976 | Pounds |
| 3,974,833 | A | | 8/1976 | Durden, III |
| 4,014,343 | A | | 3/1977 | Esty |
| 4,032,738 | A | | 6/1977 | Esty et al. |
| 4,034,761 | A | | 7/1977 | Prater et al. |

(Continued)

FOREIGN PATENT DOCUMENTS

DE 24 29 021 A1 1/1976

(Continued)

OTHER PUBLICATIONS

International Search Report from PCT/US03/37111.

(Continued)

*Primary Examiner*—Michael Peffley
*Assistant Examiner*—Alex Toy (57) ABSTRACT

An electrosurgical pencil is provided and includes an elongate housing, an electrocautery blade supported within the housing and extending distally from the housing. The electrocautery blade is connected to a source of electrosurgical energy. The pencil also includes an activation button supported on the housing, the activation button being configured and adapted to complete a control loop extending from the source of electrosurgical energy upon actuation thereof. The electrosurgical pencil further includes a manually operated aspirating/irrigating system operatively connected to the housing, wherein the aspirating/irrigating system is configured and adapted to deliver a quantity of fluid to a target surgical site and/or withdraw a quantity of fluid from the target surgical site.

32 Claims, 8 Drawing Sheets

U.S. PATENT DOCUMENTS

| | | |
|---|---|---|
| 4,038,984 A | 8/1977 | Sittner |
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A * | 11/1986 | Hasselbrack ............... 600/571 |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,796,623 A * | 1/1989 | Krasner et al. ............. 606/166 |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,605 A | 1/1993 | Imonti |
| 5,190,517 A | 3/1993 | Zieve et al. |
| 5,190,541 A * | 3/1993 | Abele et al. ............... 606/46 |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A * | 10/1993 | Rigby et al. ............... 606/46 |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A * | 6/1994 | Desai ...................... 604/21 |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,423,838 A | 6/1995 | Willard |
| 5,431,645 A | 7/1995 | Smith et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,468,240 A | 11/1995 | Gentelia et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |
| 5,486,162 A | 1/1996 | Brumbach |
| 5,496,314 A | 3/1996 | Eggers |
| 5,498,654 A | 3/1996 | Shimasaki et al. |
| D370,731 S | 6/1996 | Corace et al. |

| Patent | Date | Name |
|---|---|---|
| 5,531,722 A | 7/1996 | Van Hale |
| 5,549,604 A | 8/1996 | Sutcu et al. |
| 5,561,278 A | 10/1996 | Rutten |
| 5,599,346 A * | 2/1997 | Edwards et al. ............... 606/41 |
| 5,601,224 A | 2/1997 | Bishop et al. |
| 5,609,573 A | 3/1997 | Sandock |
| 5,626,575 A | 5/1997 | Crenner |
| 5,630,426 A | 5/1997 | Eggers et al. |
| 5,630,812 A | 5/1997 | Ellman et al. |
| 5,633,578 A | 5/1997 | Eggers et al. |
| 5,634,912 A | 6/1997 | Injev |
| 5,634,935 A * | 6/1997 | Taheri ........................ 606/190 |
| 5,643,256 A | 7/1997 | Urueta |
| D384,148 S | 9/1997 | Monson |
| 5,669,907 A | 9/1997 | Platt, Jr. et al. |
| 5,674,219 A | 10/1997 | Monson et al. |
| 5,693,044 A | 12/1997 | Cosmescu |
| 5,693,050 A | 12/1997 | Speiser |
| 5,693,052 A | 12/1997 | Weaver |
| 5,697,926 A | 12/1997 | Weaver |
| 5,702,360 A | 12/1997 | Dieras et al. |
| 5,702,387 A | 12/1997 | Arts et al. |
| 5,712,543 A | 1/1998 | Sjostrom |
| 5,713,895 A | 2/1998 | Lontine et al. |
| 5,720,745 A | 2/1998 | Farin et al. |
| D393,067 S | 3/1998 | Geary et al. |
| 5,749,869 A | 5/1998 | Lindenmeier et al. |
| 5,765,418 A | 6/1998 | Rosenberg |
| 5,776,092 A | 7/1998 | Farin et al. |
| 5,788,688 A | 8/1998 | Bauer et al. |
| 5,797,907 A | 8/1998 | Clement |
| 5,800,431 A | 9/1998 | Brown |
| 5,836,897 A | 11/1998 | Sakurai et al. |
| 5,836,909 A | 11/1998 | Cosmescu |
| 5,836,944 A | 11/1998 | Cosmescu |
| D402,030 S | 12/1998 | Roberts et al. |
| D402,031 S | 12/1998 | Roberts et al. |
| 5,843,109 A | 12/1998 | Mehta et al. |
| 5,846,236 A | 12/1998 | Lindenmeier et al. |
| 5,859,527 A | 1/1999 | Cook |
| 5,868,768 A | 2/1999 | Wicherski et al. |
| 5,876,400 A | 3/1999 | Songer |
| 5,879,347 A * | 3/1999 | Saadat ........................ 606/28 |
| 5,888,200 A | 3/1999 | Walen |
| 5,893,848 A | 4/1999 | Negus et al. |
| 5,893,849 A | 4/1999 | Weaver |
| 5,893,862 A | 4/1999 | Pratt et al. |
| 5,913,864 A | 6/1999 | Garito et al. |
| 5,919,219 A | 7/1999 | Knowlton |
| 5,928,159 A | 7/1999 | Eggers et al. |
| 5,938,589 A | 8/1999 | Wako et al. |
| 5,941,887 A | 8/1999 | Steen et al. |
| 5,944,737 A | 8/1999 | Tsonton et al. |
| 5,951,548 A | 9/1999 | DeSisto et al. |
| 5,951,581 A | 9/1999 | Saadat et al. |
| 5,954,686 A | 9/1999 | Garito et al. |
| 5,972,007 A | 10/1999 | Sheffield et al. |
| 6,004,318 A | 12/1999 | Garito et al. |
| 6,004,333 A | 12/1999 | Sheffield et al. |
| 6,004,335 A | 12/1999 | Vaitekunas et al. |
| 6,010,499 A | 1/2000 | Cobb |
| 6,022,347 A | 2/2000 | Lindenmeier et al. |
| 6,045,564 A | 4/2000 | Walen |
| 6,063,050 A | 5/2000 | Manna et al. |
| 6,068,603 A * | 5/2000 | Suzuki ........................ 600/565 |
| 6,068,627 A | 5/2000 | Orszulak et al. |
| 6,070,444 A | 6/2000 | Lontine et al. |
| 6,071,281 A | 6/2000 | Burnside et al. |
| 6,074,386 A | 6/2000 | Goble et al. |
| 6,074,387 A | 6/2000 | Heim et al. |
| 6,086,544 A | 7/2000 | Hibner et al. |
| 6,090,123 A | 7/2000 | Culp et al. |
| 6,099,525 A | 8/2000 | Cosmescu |
| 6,117,134 A | 9/2000 | Cunningham et al. |
| 6,139,547 A | 10/2000 | Lontine et al. |
| D433,752 S | 11/2000 | Saravia |
| 6,142,995 A | 11/2000 | Cosmescu |
| 6,146,353 A | 11/2000 | Platt, Jr. |
| 6,149,648 A | 11/2000 | Cosmescu |
| 6,156,035 A | 12/2000 | Songer |
| 6,197,024 B1 | 3/2001 | Sullivan |
| 6,200,311 B1 | 3/2001 | Danek et al. |
| D441,077 S | 4/2001 | Garito et al. |
| 6,213,999 B1 | 4/2001 | Platt, Jr. et al. |
| 6,214,003 B1 | 4/2001 | Morgan et al. |
| 6,238,388 B1 | 5/2001 | Ellman et al. |
| 6,241,723 B1 | 6/2001 | Heim et al. |
| 6,241,753 B1 | 6/2001 | Knowlton |
| 6,249,706 B1 | 6/2001 | Sobota et al. |
| 6,251,110 B1 | 6/2001 | Wampler |
| 6,257,241 B1 | 7/2001 | Wampler |
| 6,258,088 B1 | 7/2001 | Tzonev et al. |
| 6,273,862 B1 | 8/2001 | Privitera et al. |
| 6,277,083 B1 | 8/2001 | Eggers et al. |
| 6,287,305 B1 | 9/2001 | Heim et al. |
| 6,287,344 B1 | 9/2001 | Wampler et al. |
| 6,312,441 B1 | 11/2001 | Deng |
| 6,325,799 B1 | 12/2001 | Goble |
| D453,222 S | 1/2002 | Garito et al. |
| D453,833 S | 2/2002 | Hess |
| 6,350,276 B1 | 2/2002 | Knowlton |
| 6,352,544 B1 * | 3/2002 | Spitz ........................ 606/159 |
| 6,355,034 B2 | 3/2002 | Cosmescu |
| 6,358,281 B1 | 3/2002 | Berrang et al. |
| 6,361,532 B1 | 3/2002 | Burek |
| D457,955 S | 5/2002 | Bilitz |
| 6,395,001 B1 | 5/2002 | Ellman et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,725 B1 | 6/2002 | Khandkar et al. |
| 6,413,255 B1 | 7/2002 | Stern |
| 6,416,491 B1 | 7/2002 | Edwards et al. |
| 6,416,509 B1 | 7/2002 | Goble et al. |
| 6,425,912 B1 | 7/2002 | Knowlton |
| 6,458,122 B1 | 10/2002 | Pozzato |
| 6,458,125 B1 | 10/2002 | Cosmescu |
| 6,461,352 B2 | 10/2002 | Morgan et al. |
| 6,464,702 B2 | 10/2002 | Schulze et al. |
| 6,471,659 B2 | 10/2002 | Eggers et al. |
| 6,494,882 B1 | 12/2002 | Lebouitz et al. |
| 6,500,169 B1 | 12/2002 | Deng |
| 6,511,479 B2 | 1/2003 | Gentelia et al. |
| 6,526,320 B2 * | 2/2003 | Mitchell ........................ 607/101 |
| 6,551,313 B1 | 4/2003 | Levin |
| 6,558,383 B2 | 5/2003 | Cunningham et al. |
| 6,585,664 B2 | 7/2003 | Burdorff et al. |
| 6,589,239 B2 | 7/2003 | Khandkar et al. |
| 6,610,054 B1 | 8/2003 | Edwards et al. |
| 6,610,057 B1 | 8/2003 | Ellman et al. |
| 6,616,658 B2 | 9/2003 | Ineson |
| 6,618,626 B2 | 9/2003 | West, Jr. et al. |
| 6,620,161 B2 | 9/2003 | Schulze et al. |
| 6,632,193 B1 | 10/2003 | Davison et al. |
| 6,652,514 B2 | 11/2003 | Ellman et al. |
| 6,662,053 B2 | 12/2003 | Borkan |
| 6,669,691 B1 | 12/2003 | Taimisto |
| 6,685,701 B2 | 2/2004 | Orszulak et al. |
| 6,685,704 B2 | 2/2004 | Greep |
| 6,702,812 B2 | 3/2004 | Cosmescu |
| 6,712,813 B2 | 3/2004 | Ellman et al. |
| 6,740,079 B1 | 5/2004 | Eggers et al. |
| 6,747,218 B2 | 6/2004 | Huseman et al. |
| D493,530 S | 7/2004 | Reschke |
| D493,888 S | 8/2004 | Reschke |

| | | | | | | |
|---|---|---|---|---|---|---|
| D494,270 S | 8/2004 | Reschke | | 2004/0030330 A1 | 2/2004 | Brassell et al. |
| D495,051 S | 8/2004 | Reschke | | 2004/0030332 A1 | 2/2004 | Knowlton et al. |
| D495,052 S | 8/2004 | Reschke | | 2004/0034346 A1 | 2/2004 | Stern et al. |
| 6,794,929 B2 | 9/2004 | Pelly | | 2004/0054370 A1 | 3/2004 | Given |
| 6,830,569 B2 | 12/2004 | Thompson et al. | | 2004/0092927 A1 | 5/2004 | Podhajsky et al. |
| 6,840,948 B2 | 1/2005 | Albrecht et al. | | 2004/0111087 A1 | 6/2004 | Stern et al. |
| 6,855,140 B2 | 2/2005 | Albrecht et al. | | 2004/0124964 A1 | 7/2004 | Wang et al. |
| 6,902,536 B2 | 6/2005 | Manna et al. | | 2004/0127889 A1 | 7/2004 | Zhang et al. |
| 6,905,496 B1 | 6/2005 | Ellman et al. | | 2004/0143677 A1 | 7/2004 | Novak |
| 6,923,804 B2 | 8/2005 | Eggers et al. | | 2004/0147909 A1 | 7/2004 | Johnston et al. |
| 6,923,809 B2 | 8/2005 | Eggers et al. | | 2004/0162553 A1 | 8/2004 | Peng et al. |
| 6,939,347 B2 | 9/2005 | Thompson | | 2004/0167512 A1 | 8/2004 | Stoddard et al. |
| 6,955,674 B2 | 10/2005 | Eick et al. | | 2004/0172011 A1 | 9/2004 | Wang et al. |
| 2001/0047183 A1 | 11/2001 | Privitera et al. | | 2004/0172015 A1 | 9/2004 | Novak |
| 2001/0049524 A1 | 12/2001 | Morgan et al. | | 2004/0172016 A1 | 9/2004 | Bek et al. |
| 2002/0019596 A1 | 2/2002 | Eggers et al. | | 2004/0181140 A1 | 9/2004 | Falwell et al. |
| 2002/0019631 A1 | 2/2002 | Kidder et al. | | 2004/0230262 A1 | 11/2004 | Sartor et al. |
| 2002/0022838 A1 | 2/2002 | Cunningham et al. | | 2004/0236323 A1 | 11/2004 | Schoenman et al. |
| 2002/0026145 A1* | 2/2002 | Bagaoisan et al. ....... 604/96.01 | | 2004/0243120 A1 | 12/2004 | Orszulak et al. |
| 2002/0035364 A1 | 3/2002 | Schoenman et al. | | 2004/0267252 A1 | 12/2004 | Washington et al. |
| 2002/0049427 A1 | 4/2002 | Wiener et al. | | 2004/0267254 A1 | 12/2004 | Manzo et al. |
| 2002/0058958 A1 | 5/2002 | Walen | | 2004/0267297 A1 | 12/2004 | Malackowski |
| 2002/0087079 A1 | 7/2002 | Culp et al. | | 2005/0033286 A1 | 2/2005 | Eggers et al. |
| 2002/0095199 A1 | 7/2002 | West, Jr. et al. | | 2005/0059858 A1 | 3/2005 | Frith et al. |
| 2002/0103485 A1* | 8/2002 | Melnyk et al. ................. 606/45 | | 2005/0059967 A1 | 3/2005 | Breazeale, Jr. et al. |
| 2002/0111622 A1 | 8/2002 | Khandkar et al. | | 2005/0065510 A1 | 3/2005 | Carmel et al. |
| 2002/0133148 A1* | 9/2002 | Daniel et al. .................. 606/34 | | 2005/0070891 A1 | 3/2005 | DeSisto |
| 2002/0151886 A1* | 10/2002 | Wood .......................... 606/41 | | 2005/0085804 A1 | 4/2005 | McGaffigan |
| 2002/0151887 A1 | 10/2002 | Stern et al. | | 2005/0096645 A1 | 5/2005 | Wellman et al. |
| 2002/0156471 A1 | 10/2002 | Stern et al. | | 2005/0096646 A1 | 5/2005 | Wellman et al. |
| 2002/0173776 A1 | 11/2002 | Batchelor et al. | | 2005/0107782 A1 | 5/2005 | Reschke |
| 2002/0198519 A1 | 12/2002 | Qin et al. | | 2005/0113817 A1 | 5/2005 | Isaacson et al. |
| 2003/0004508 A1 | 1/2003 | Morgan et al. | | 2005/0113818 A1 | 5/2005 | Sartor et al. |
| 2003/0014043 A1 | 1/2003 | Henry et al. | | 2005/0113823 A1 | 5/2005 | Reschke et al. |
| 2003/0032950 A1 | 2/2003 | Altshuler et al. | | 2005/0113824 A1 | 5/2005 | Sartor et al. |
| 2003/0050633 A1 | 3/2003 | Ellman | | 2005/0113825 A1 | 5/2005 | Cosmescu |
| 2003/0055421 A1* | 3/2003 | West et al. .................... 606/41 | | 2005/0149001 A1 | 7/2005 | Uchikubo et al. |
| 2003/0065321 A1 | 4/2003 | Carmel et al. | | 2005/0154385 A1 | 7/2005 | Heim et al. |
| 2003/0078572 A1 | 4/2003 | Pearson et al. | | 2006/0041257 A1 | 2/2006 | Sartor et al. |
| 2003/0083655 A1 | 5/2003 | Van Wyk | | 2006/0058783 A1 | 3/2006 | Buchman |
| 2003/0088247 A1 | 5/2003 | Ineson | | | | |
| 2003/0109864 A1 | 6/2003 | Greep et al. | | | | |
| 2003/0109865 A1 | 6/2003 | Greep et al. | | | | |
| 2003/0130663 A1 | 7/2003 | Walen | | | | |
| 2003/0144680 A1 | 7/2003 | Kellogg et al. | | | | |
| 2003/0163125 A1 | 8/2003 | Greep | | | | |
| 2003/0199856 A1 | 10/2003 | Hill et al. | | | | |
| 2003/0199866 A1 | 10/2003 | Stern et al. | | | | |
| 2003/0199869 A1 | 10/2003 | Johnson et al. | | | | |
| 2003/0212393 A1 | 11/2003 | Knowlton et al. | | | | |
| 2003/0212397 A1 | 11/2003 | Avrahami et al. | | | | |
| 2003/0216728 A1 | 11/2003 | Stern et al. | | | | |
| 2003/0220635 A1 | 11/2003 | Knowlton et al. | | | | |
| 2003/0220638 A1 | 11/2003 | Metzger | | | | |
| 2003/0225401 A1 | 12/2003 | Eggers et al. | | | | |
| 2003/0229341 A1 | 12/2003 | Albrecht et al. | | | | |
| 2003/0229343 A1 | 12/2003 | Albrecht et al. | | | | |
| 2004/0000316 A1 | 1/2004 | Knowlton et al. | | | | |
| 2004/0002704 A1 | 1/2004 | Knowlton et al. | | | | |
| 2004/0002705 A1 | 1/2004 | Knowlton et al. | | | | |
| 2004/0010246 A1 | 1/2004 | Takahashi | | | | |
| 2004/0015160 A1 | 1/2004 | Lovewell | | | | |
| 2004/0015161 A1 | 1/2004 | Lovewell | | | | |
| 2004/0015162 A1 | 1/2004 | McGaffigan | | | | |
| 2004/0015216 A1 | 1/2004 | DeSisto | | | | |
| 2004/0024395 A1 | 2/2004 | Ellman et al. | | | | |
| 2004/0024396 A1 | 2/2004 | Eggers | | | | |
| 2004/0030328 A1 | 2/2004 | Eggers et al. | | | | |

FOREIGN PATENT DOCUMENTS

| | | |
|---|---|---|
| DE | 30 45 996 | 7/1982 |
| EP | 0 186 369 A | 7/1986 |
| EP | 1050277 | 11/2000 |
| EP | 1050279 | 11/2000 |
| EP | 1082945 | 3/2001 |
| EP | 1293171 | 3/2003 |
| FR | 2235669 | 1/1975 |
| WO | WO94/20032 | 9/1994 |
| WO | WO 96/39086 | 12/1996 |
| WO | WO 98/43264 | 10/1998 |
| WO | WO01/64122 | 9/2001 |
| WO | WO 02/47568 A1 | 6/2002 |
| WO | WO 2004/010883 A1 | 2/2004 |
| WO | WO 2004/073753 A2 | 9/2004 |
| WO | WO 2005/060849 A1 | 7/2005 |

OTHER PUBLICATIONS

International Search Report from PCT/US04/04685.
International Search Report from EP/0401/5980.
International Search Report from PCT/US03/22900.
ISR from EP 05019882.9 dated Feb. 16, 2006.
ISR from EP 05021777.7 dated Feb. 23, 2006.
International Search Report from EP 06 01 4431 dated Oct. 31, 2006.

* cited by examiner

PISTOL GRIP ELECTROSURGICAL PENCIL WITH MANUAL ASPIRATOR/IRRIGATOR AND METHODS OF USING THE SAME

BACKGROUND

1. Technical Field

The present disclosure relates generally to electrosurgical instruments and, more particularly, to an electrosurgical pencil having an integral manual aspirator/irrigator. The present disclosure is also directed to methods of using the electrosurgical pencils disclosed herein.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical fulguration.

In particular, electrosurgical fulguration includes the application of electric spark to biological tissue, for example, human flesh or the tissue of internal organs, without significant cutting. The spark is produced by bursts of radio-frequency electrical energy generated from an appropriate electrosurgical generator. Generally, fulguration is used to coagulate, cut or blend body tissue. Coagulation is defined as a process of desiccating tissue wherein the tissue cells are ruptured and dehydrated/dried. Electrosurgical cutting, on the other hand, includes applying an electrical spark to tissue in order to produce a cutting or dividing effect. Blending includes the function of cutting combined with the production of a hemostasis effect.

As used herein the term "electrosurgical pencil" is intended to include instruments which have a handpiece which is attached to an active electrode and which is used to cauterize, coagulate, blend and/or cut tissue. Typically, the electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (e.g., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material.

During surgery, these electrosurgical instruments generally produce a plume (typically of smoke) when organic material (e.g., the tissue of the patient) is being vaporized. The plume created by the vaporization of the organic material is offensive in the operating room and especially if inhaled.

In the typical technique, the plume is aspirated by a conventional suction tube being held near the site of the electrosurgical procedure by an assistant. Unfortunately, this method inefficiently requires the full time attention of the assistant and the placement of the often bulky suction tube in the operative field of the surgeon thus obstructing the surgeon's view. Additionally, these suction tubes typically operate on a continuous basis and create substantial noise levels during surgery thus potentially interfering with normal operating room dialogue.

Accordingly, electrosurgical instruments including integrated systems for aspirating the plume produced by the electrosurgical instruments during the electrosurgical procedures as well as for aspirating excess blood of bodily fluids prior to coagulating the remaining vessels have been developed. For example, electrosurgical instruments have been developed which include an aspirating system including a suction tube having at least one suction opening disposed in close proximity to the electrocautery tip (e.g., a blade, loop, etc.) a proximal end which is in fluid communication with a remote source of vacuum. In order to reduce the potential of the suction tube from becoming tangled or interfering with the movement of the operating staff around the operating room, the source of vacuum is place close to the operative site thus keeping the suction tube shorter. As a result, the noise from the source of vacuum is also closer to the operative site and thus continues to potentially interfere with the normal operating room dialogue.

It is an object of the present disclosure to provide an electrosurgical pencil including a manual aspirator/irrigator.

It is another object of the present disclosure to provide an electrosurgical instrument including a self-contained manual aspirator/irrigator.

It is a further object of the present disclosure to provide an electrosurgical instrument having a manual aspirator/irrigator which effectively removes a plume created during surgical procedures and which effectively delivers a fluid during the surgical procedures.

It is still a further object of the present disclosure to provide an electrosurgical instrument having a manual aspirator/irrigator which can deliver a quantity of irrigating solution and/or medicament during the surgical procedure.

These and other objects will be more clearly illustrated below by the description of the drawings and the detailed description of the preferred embodiments.

SUMMARY

The present disclosure is directed to an electrosurgical pencil having an aspirating/irrigating system. According to one aspect of the present disclosure, the electrosurgical pencil includes an elongate housing, an electrocautery blade supported within the housing and extending distally from the housing, the electrocautery blade being connected to a source of electrosurgical energy, and an activation button supported on the housing, the activation button being configured and adapted to complete a control loop extending from the source of electrosurgical energy upon actuation thereof. The electrosurgical pencil further includes an aspirating/irrigating system operatively connected to the housing, wherein the aspirating/irrigating system is configured and adapted to manually perform at least one of delivering a quantity of fluid to a target surgical site and withdrawing a quantity of fluid from the target surgical site.

It is envisioned that the aspirating/irrigating system includes a resilient or compliant handle which defines at least one chamber therein. The aspirating/irrigating system can further include a fluid passage extending between at least one chamber of the resilient handle and at least one aperture formed in a distal end of the housing. A quantity of fluid is contained within the at least one chamber of the resilient or compliant handle.

The handle has an expanded condition and is compressible to a non-expanded condition, wherein compression of the resilient handle causes the quantity of fluid contained in the at least one chamber of the resilient handle to be urged through the fluid passage and out of at least one aperture formed in the distal end of the housing. Accordingly, when the resilient handle is allowed to return to its expanded condition from the non-expanded condition, fluid is drawn into the at least one chamber of the resilient handle through the fluid passage and in through at least one aperture formed in the distal end of the housing.

The aspirating/irrigating system preferably further includes a valve disposed between at least one fluid passage and at least one fluid chamber. The valve is configured and adapted to allow fluid to pass from the chamber to the fluid passage when the resilient handle is compressed to a non-expanded condition. The aspirating/irrigating system preferably further includes a second valve disposed in fluid communication with a second chamber. The second valve is configured and adapted to allow fluid to pass into the second chamber when the resilient handle is allowed to return to its expanded condition. The second valve is disposed between a second chamber in the handle and a second passage which communicates with at least one aperture at the distal end of the housing. Preferably, the resilient handle is fabricated rubber.

It is envisioned that the electrosurgical pencil further includes a mode selector supported on the housing, the mode selector being electrically connected to the source of electrosurgical energy and is configured and adapted to vary a waveform duty cycle which is delivered from the source of electrosurgical energy to the electrocautery blade. The mode selector is configured and adapted to vary the waveform duty cycle to produce at least one of a cutting, blending and coagulating effect.

In another embodiment, the aspirating/irrigating system includes a resilient handle and defines first and second chambers separated by a dividing member, and first and second fluid passages extending respectively between the first and second chambers of the resilient handle and the at least one aperture formed in a distal end of the housing. The handle has an expanded condition and is compressible to a non-expanded condition.

The aspirating/irrigating system includes a first valve disposed between the first fluid passage and the first chamber, a second valve disposed between the second fluid passage and the second chamber, and a relief valve for equalizing the environmental conditions between the first and second chambers.

The first chamber preferably includes a quantity of fluid contained therein. The first valve is configured and adapted to allow the quantity of fluid contained in the first chamber to pass from the first chamber to the first fluid passage when the resilient handle is compressed to a non-expanded condition. The second valve is configured and adapted to allow fluid to be drawn into the second chamber when the resilient handle is allowed to return to the expanded condition from the non-expanded condition.

According to another aspect of the present disclosure, an electrosurgical pencil for selectively providing electrosurgical energy to tissue, the electrosurgical pencil having an electrosurgical blade electrically connected to the source of electrosurgical energy is provided. The electrosurgical pencil includes an elongate housing configured and adapted to receive the electrosurgical blade in a distal end thereof, and a self-contained, manual aspirating/irrigating system operatively connected to the housing. The aspirating/irrigating system includes a body portion defining at least one chamber therein, and a fluid passage extending between an aperture formed in a distal end of the housing and the at least one chamber, wherein the body portion has an expanded condition in which at least one chamber has a first volume and a non-expanded condition in which at least one chamber has a second volume which is less than the first volume.

The aspirating/irrigating system includes a first valve disposed between at least one chamber and the fluid passage, and a second valve disposed in the body portion and in fluid communication with at least one chamber. The first valve is configured and adapted to allow fluid to pass out of at least one chamber and the second valve is configured and adapted to allow fluid to enter at least one chamber.

At least one chamber of the body portion contains a quantity of fluid. Accordingly, when the body portion is compressed from the first volume to the second volume the quantity of fluid is urged out of one of the chambers through the first valve and when the body portion is allowed to return to the first volume from the second volume fluid enters a different one of the chambers from the second valve.

According to yet another aspect of the present disclosure, a method of aspirating/irrigating a target surgical site during an electrosurgical procedure is provided. The method includes the step of providing an electrosurgical pencil including an elongate housing, an electrocautery blade supported within the housing and extending distally from the housing, the electrocautery blade being connected to a source of electrosurgical energy, an activation button supported on the housing, the activation button being configured and adapted to complete a control loop extending from the source of electrosurgical energy upon actuation thereof, and an aspirating/irrigating system operatively connected to the housing, wherein the aspirating/irrigating system includes a resilient handle which is configured and adapted to at least one of deliver a quantity of fluid contained in the handle to a target surgical site when the handle is compressed and withdraw a quantity of fluid from the target surgical site when the handle is allowed to expand.

The method further includes the steps of performing an electrocautery function at a target surgical site, and at least one of compressing the handle to deliver the quantity of fluid contained therein to the target surgical site and allowing the handle to expand to withdraw a quantity of fluid from the target surgical site.

It is envisioned that the aspirating/irrigating system includes a fluid passage extending between an aperture formed in a distal end of the housing and the at least one chamber.

With the handle at least partially compressed, the method further includes the step of placing the aperture in a quantity of fluid and allowing the handle to expand to withdraw fluid into the at least one chamber.

These and other features and advantages of the present disclosure will be readily apparent from the following drawings and detailed description of preferred embodiments.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Preferred embodiments of the presently disclosed electrosurgical pencil will now be described in detail with reference to the drawing figures wherein like reference numerals identify similar or identical elements. As used herein, the term "distal" refers to that portion which is further from the user while the term "proximal" refers to that portion which is closer to the user.

Figure 1:
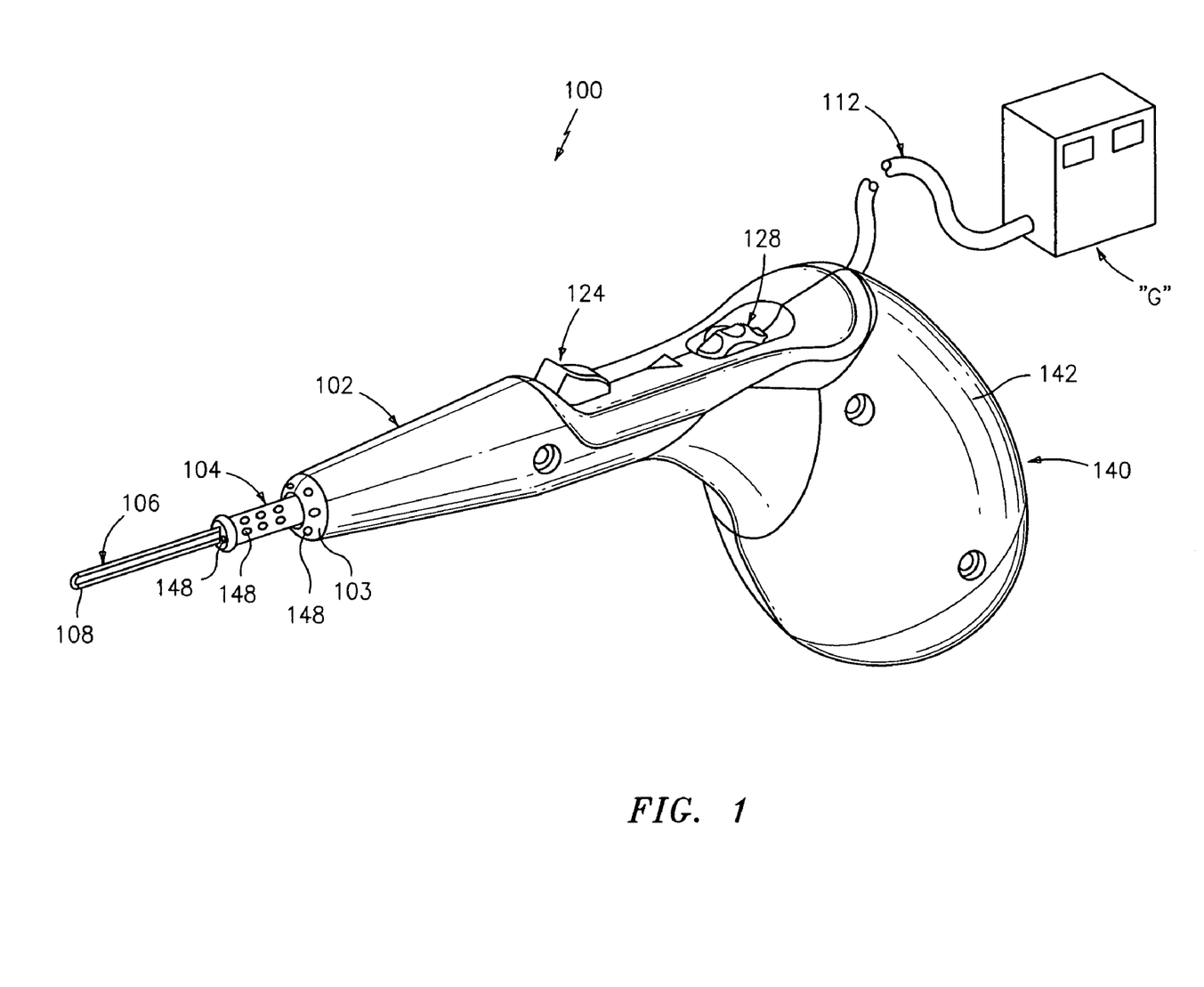
FIG. 1 is a perspective view of an electrosurgical pencil in accordance with the present disclosure.

FIG. 1 sets forth a perspective view of an electrosurgical pencil constructed in accordance with one embodiment of the present disclosure and generally referenced by numeral 100. While the following description will be directed towards electrosurgical pencils it is envisioned that the features and concepts of the present disclosure can be applied to any electrosurgical type instrument.

As seen in FIGS. 1-5, electrosurgical pencil 100 includes an elongate housing 102 configured and adapted to support a blade receptacle 104 at a distal end 103 thereof which, in turn, receives a replaceable electrocautery end effector 106 in the form of a loop and/or blade therein. The term electrocautery blade, as used herein, is understood to include a planar blade, a loop (as shown in FIGS. 1-5), a needle, etc. A distal end portion 108 of blade 106 extends distally from receptacle 104 while a proximal end portion 110 (see FIG. 5) is retained within distal end 103 of housing 102. It is contemplated that electrocautery blade 106 is fabricated from a conductive type material, such as, for example, stainless steel, or is coated with an electrically conductive material.

As shown in FIG. 1, electrosurgical pencil 100 is coupled to a conventional electrosurgical generator "G" via a cable 112. Cable 112 includes a transmission wire (see FIG. 5) which electrically interconnects electrosurgical generator "G" with the proximal end portion of electrocautery blade 106. Cable 112 further includes a control loop 116 which electrically interconnects activation buttons, supported on an outer surface 107 of housing 102, with electrosurgical generator "G".

Reference is made to commonly assigned U.S. Provisional Patent No. 60/413,410 filed Sep. 25, 2002; U.S. Provisional Patent No. 60/424,352 filed Nov. 5, 2002; and U.S. Provisional Patent No. 60/448,520 filed Feb. 20, 2003, the entire contents of each of which are incorporated herein by reference, for a more detailed explanation and for alternative configurations of control loop 107.

By way of example only, electrosurgical generator "G" may be any one of the following, or equivalents thereof: the "FORCE FX", "FORCE 2" or "FORCE 4" generators manufactured by Valleylab, Inc., a division of Tyco Healthcare, LP, located in Boulder, Colo. Preferably, electrosurgical generator "G" can be variable in order to provide appropriate first RF signals (e.g., 1 to 120 watts) for tissue cutting and appropriate second RF signals (e.g., 1 to 300 watts) for tissue coagulation. Generator "G" may also include a "blend" mode.

Preferably, an exemplary electrosurgical generator "G" is disclosed in commonly assigned U.S. Pat. No. 6,068,627 to Orszulak, et al., the entire contents of which is hereby incorporated by reference. The electrosurgical generator disclosed in the '627 patent includes, inter alia, an identifying circuit and a switch therein. In general, the identifying circuit is responsive to information received from a generator and transmits a verification signal back to the generator. Meanwhile, the switch is connected to the identifying circuit and is responsive to signaling received from the identifying circuit.

Turning back to FIGS. 1-5, as mentioned above, electrosurgical pencil 100 further includes at least one activation button 124 supported on outer surface 107 of housing 102. Activation button 124 is operatively connected to a switch 126 which, in turn, controls the transmission of RF electrical energy supplied from generator "G" to electrosurgical blade 106, in the manner of and on/off switch. More particularly, switch 126 is electrically coupled to control loop 116 and is configured to close and/or complete control loop 116 to thereby permit RF energy to be transmitted to electrocautery blade 106 from electrosurgical generator "G". It is envisioned that activation button 124 may be multi-positionable such that a "low" setting and a "high" setting for each mode is available to the surgeon for each mode.

Figures 2, 3:
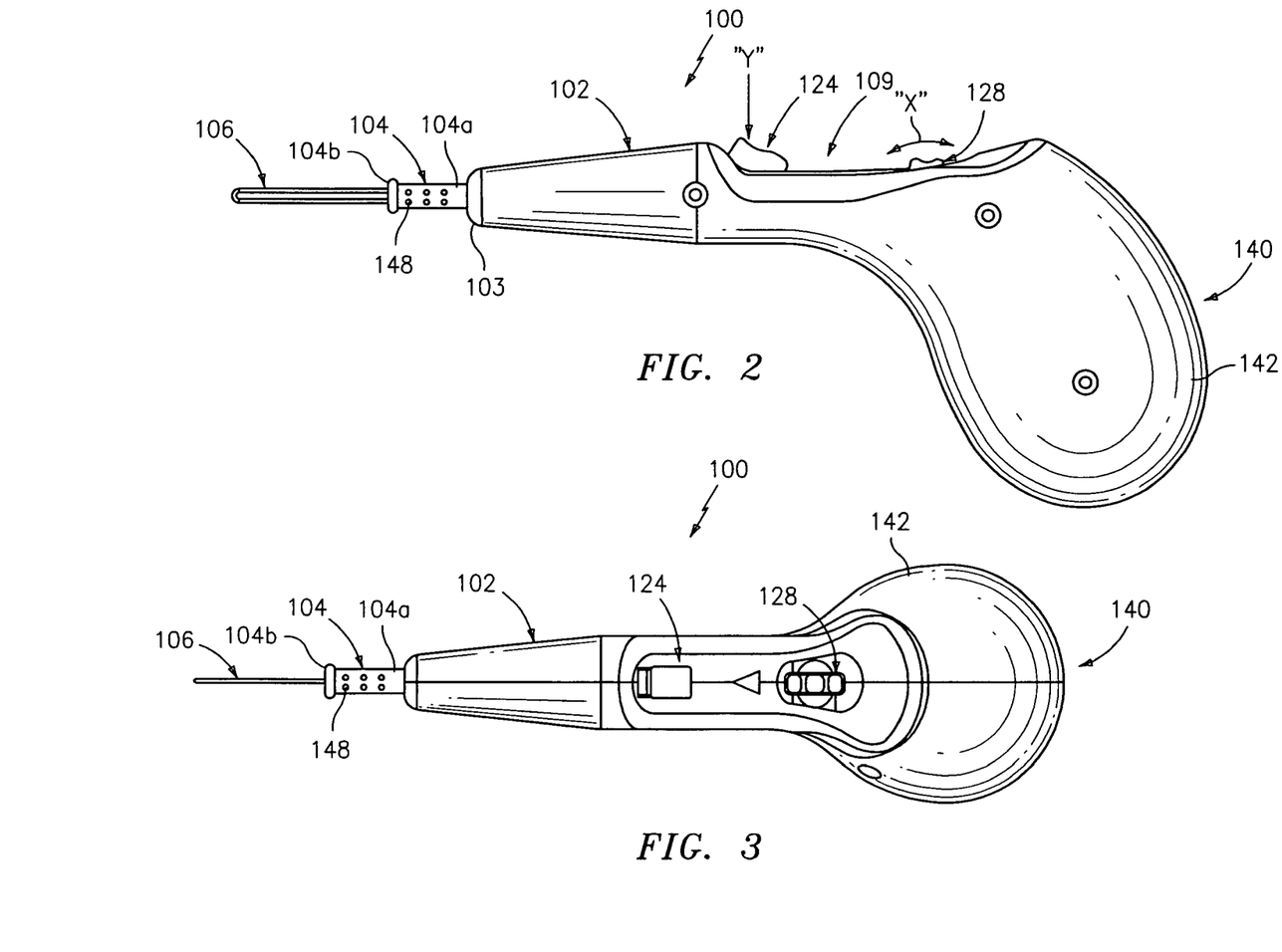
FIG. 2 is a side elevational view of the electrosurgical pencil of FIG. 1.
FIG. 3 is a top plan view of the electrosurgical pencil of FIG. 1.
Figures 4, 5:
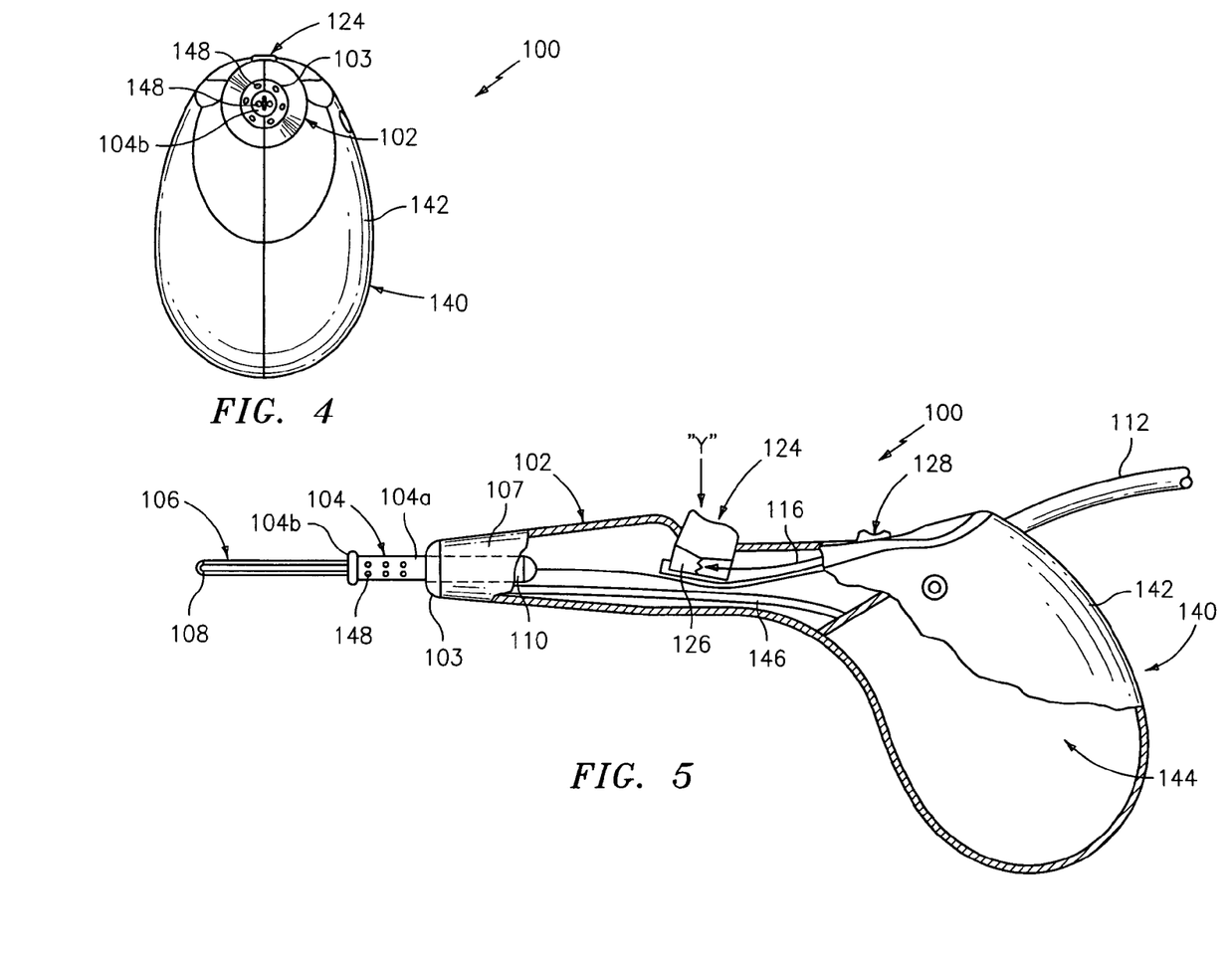
FIG. 4 is a front elevational view of the electrosurgical pencil of FIG. 1.
FIG. 5 is a cross-sectional side elevational view of the electrosurgical pencil of FIG. 1 as taken through a longitudinal axis thereof.

Electrosurgical pencil 100 further includes at least one mode selector 128 operatively supported on housing 102. Mode selector 128 is configured and adapted to enable the surgeon to set electrosurgical pencil 100 to one of a number of discreet modes of operation, such as, for example, cutting, blending and/or coagulating. As seen in FIG. 2, mode selector 128 can be rotated in the directions indicated by double-headed arrow "X" from a first position, in which electrosurgical pencil 100 is set to transmit a cutting "waveform duty cycle" to electrocautery blade 106, to a second position, in which electrosurgical pencil 100 is set to transmit a blending "waveform duty cycle" to electrocautery blade 106, and to a third position, in which electrosurgical pencil 100 is set to transmit a coagulating "waveform duty cycle" to electrocautery blade 106.

It is contemplated that mode selector 128 may be provided with a series of cooperating discreet positions defining a series of positions, preferably three, to allow easy selection of the mode of operation of electrosurgical pencil 100 between, for example, cutting, blending and coagulating. The series of cooperating discreet or detented positions also provide the surgeon with a degree of tactile feedback.

Electrosurgical pencil 100 further includes a manual aspirating/irrigating system 140 operatively connected to a proximal end of housing 102. Aspirating/irrigating system 140 includes a handle or body portion 142 preferably fabricated from a resilient or substantially compliant material, such as, for example, rubber, and defines a hollow chamber 144 therein (see FIG. 5). Handle 142 is preferably shaped and sized to substantially fit in the palm of a surgeon's hand. Aspirating/irrigating system 140 further includes at least one fluid passage 146 extending between chamber 144 of handle 142 and aperture(s) 148 formed in at least one of a side surface 104a of blade receptacle 104 (see FIGS. 1-3 and 5), a distal surface 104b of blade receptacle 104 (see FIGS. 1 and 4) and distal end 103 of housing 102 (see FIGS. 1 and 4).

Handle 142 has a fully expanded condition and a plurality of non-expanded conditions when handle 142 is squeezed and/or compressed an amount by the surgeon. In the fully expanded condition, chamber 144 of handle 142 defines a first volume, while in one of its plurality of non-fully expanded conditions, chamber 144 of handle 142 defines a plurality of second volumes, each of which are less than the first volume. In this manner, when handle 142 is in one of the plurality of second volumes and then released, handle 142 creates a suction force at aperture(s) 148, through fluid passage 146.

When handle 142 is urged from its fully expanded condition to its non-fully expanded condition (i.e., to at least partially evacuate chamber 144), a fluid "F", contained within chamber 144 of handle 142, is urged and/or squeezed through fluid passage 146 and out through aperture(s) 148. When handle 142 is allowed to return to its fully expanded condition, from its non-fully expanded condition, (i.e., as by allowing resilient handle 142 to overcome the squeezing and/or compressing forces and to return to its fully expanded condition), as described above, a suction is created at apertures 148, through fluid passage 146, to withdraw fluid "F" into chamber 144. As used herein, and in no way is it to be considered limiting, the term fluid is understood to include air, water, saline, medicament, body fluid, blood, lymph fluid, smoke, etc.

In operation and depending on the particular electrosurgical function desired (e.g. cutting, blending or coagulating), the surgeon manipulates, e.g., rotates, mode selector 128 in direction "X" until the desired electrosurgical function is selected. The surgeon then depresses activation button 124, in the direction indicated by arrow "Y" (see FIGS. 2 and 5) thereby closing switch 126 and closing and/or completing control loop 116. In turn, generator "G" transmits an appropriate waveform output to electrocautery blade 106 via transmission wire 114.

Preferably, as seen throughout the figures, activation button 124 and mode selector 128 are supported in a recess or depression 109 formed in outer wall 107 of housing 102. Desirably, activation button 124 is positioned at a location where the fingers of the surgeon would normally rest when electrosurgical pencil 100 is held in the hand of the surgeon while mode selector 128 is placed at a location which would not be confused with activation button 124.

Moreover, depending on the particular electrosurgical procedure being performed, the stage of the procedure and the resulting effects created by electrocautery blade 106 on the body tissue, the surgeon may desire or be required to manipulate aspirating/irrigating system 140. For example, fluid produced by the body and located at the surgical site (e.g., blood, lymph fluid, etc.) during the surgical procedure can be aspirated from the surgical site using electrosurgical pencil 100. Aspiration of fluid from the surgical site can be achieved, for example with chamber 144 of handle 142 empty, by the surgeon initially squeezing and/or compressing handle 142 to at least partially evacuate chamber 144, placing aperture(s) 148 in or near a quantity of fluid "F", and allowing handle 142 to expand causing the vacuum of chamber 144 to withdraw fluid from the surgical site into chamber 144 through fluid passage 146.

Figures 6, 7:
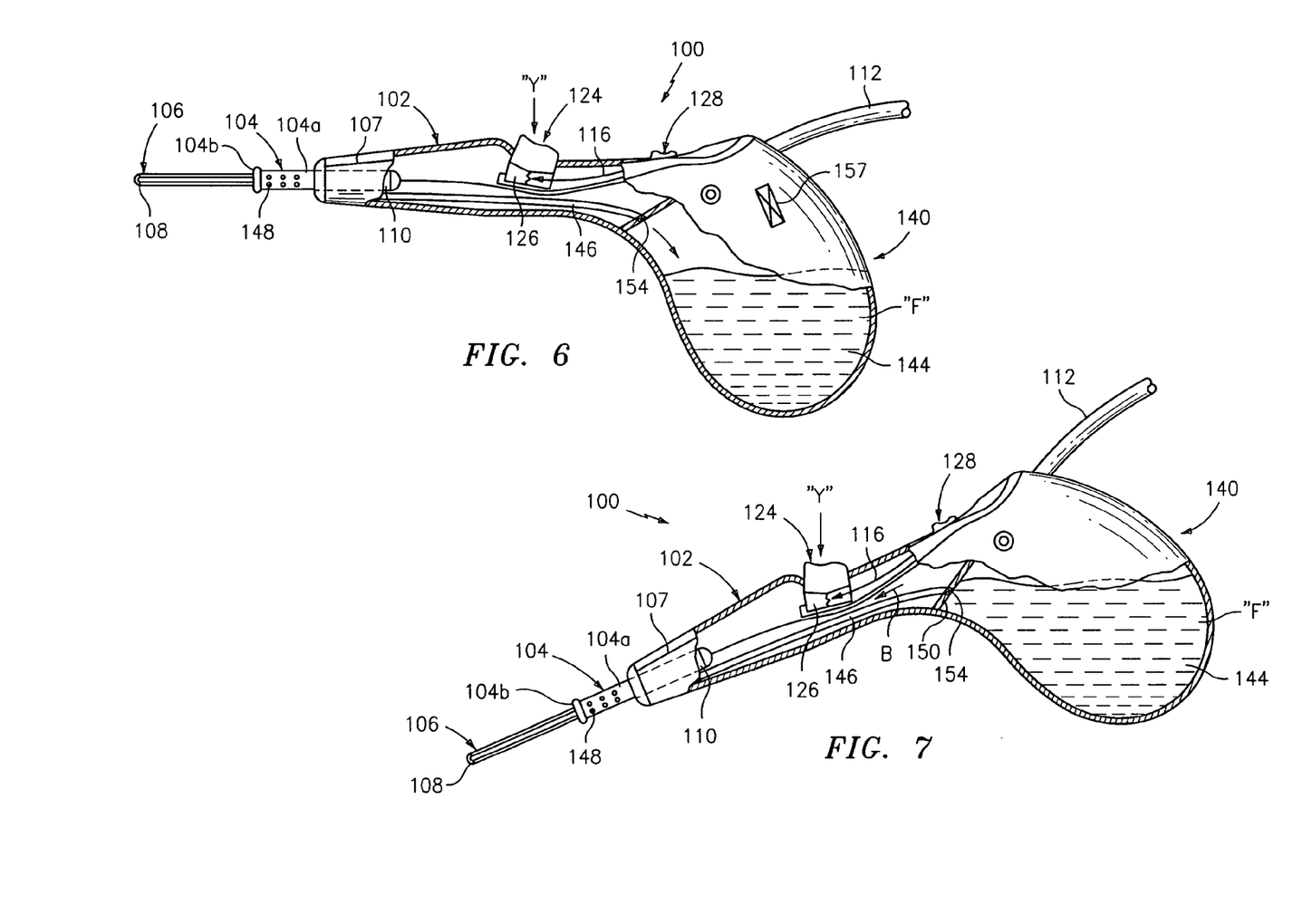
FIG. 6 is a cross-sectional side elevational view of the electrosurgical pencil of FIG. 1, illustrating a first step in a mode of operation.
FIG. 7 is a cross-sectional side elevational view of the electrosurgical pencil of FIG. 1, illustrating a second step in the mode of operation.

The aspiration step can be repeated, without first evacuating chamber 144 of fluid "F" contained therein, by first orienting and/or tilting electrosurgical pencil 100 to a position where fluid "F" contained in chamber 144 does not cover, as seen in FIG. 6, an interface 150 between chamber 144 and fluid passage 146, squeezing and/or compressing handle 142, placing aperture(s) 148 in fluid at the surgical site, and allowing handle 142 to expand.

In addition, during the surgical procedure, it may be desired or necessary to irrigate the surgical site with a fluid "F". Irrigation of the surgical site with fluid "F", can be achieved by orienting and/or tilting electrosurgical pencil 100 to a position where fluid "F", contained in chamber 144, covers (see FIG. 7) an interface 150 between chamber 144 and fluid passage 146 and by then squeezing and/or compressing handle 142 to expel a quantity of fluid "F" therefrom. It is contemplated that fluid "F" expelled from electrosurgical pencil 100 can be a saline solution for rinsing the surgical site clean or, alternatively, a medicament for treating the surgical site. Examples of medicaments which can be delivered by electrosurgical pencil 100 include, and are not limited to: coagulants; hemostats; sealants; adhesives and the like.

It is contemplated that aspirating/irrigating system 140 can include a control switch 152 incorporated into handle 142 and connected to chamber 144 and a valve 154 disposed at interface 150, between fluid passage 146 and chamber 144. Preferably, valve 154 is a one-way check-type valve which cooperates with control switch 152 to permit a unidirectional flow of fluid either into (or out of) chamber 144 through fluid passage 146 depending upon a particular purpose.

Figures 8A, 8B, 9:
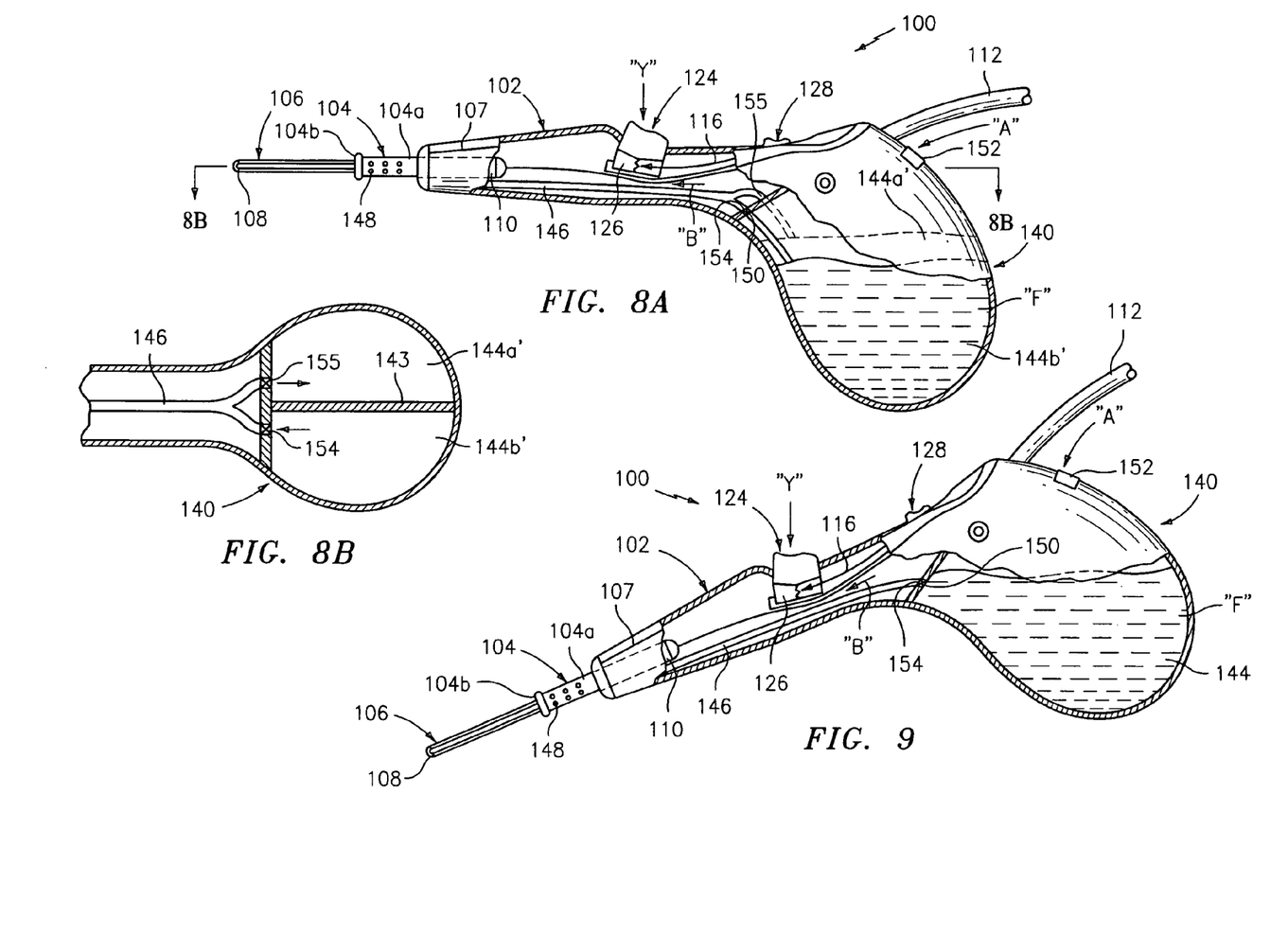
FIG. 8A is a cross-sectional side elevational view of an electrosurgical pencil, according to another embodiment of the disclosure, illustrating a first step in a mode of operation.
FIG. 8B is a bottom cross-sectional view of the electrosurgical pencil of FIG. 8A taken through Y-Y of FIG. 8A.
FIG. 9 is a cross-sectional side elevational view of the electrosurgical pencil of FIG. 8, illustrating a second step in the mode of operation.

As best seen if FIGS. 8A and 8B, it is also envisioned that the aspirating/irrigating system 140 may include two check valves 154 and 155 which are mechanically coupled between fluid passage 146 and two chambers 144a' and 144b', respectively. A divider 143 is disposed between chambers 144a' and 144b'. In this instance, fluid from chamber 144b' is utilized to irrigate that surgical site and the suction created upon irrigation (i.e., upon squeezing handle 142) is utilized to aspirate the surgical site and return surgical waste to chamber 144a' when handle 142 is released. Each check valve 154 and 155 is set up to allow passage in one direction to accomplish this purpose.

A relief valve may be utilized to restore environmental equilibrium between the two chambers 144a' and 144b' after each irrigation/aspiration cycle. Alternatively, control switch 152 may be utilized with a single check valve which allows selective flow into the chamber or out of the chamber upon activation. As can be appreciated, more than one check valve may be utilized for this purpose, i.e., a first check valve 144a' for storing liquid and contaminants from the surgical site and a second check valve 144b' for storing irrigation fluid (see FIG. 12). In this instance, two different fluid passages would be employed. This is discussed in greater detail below.

In one method of use, as seen in FIG. 7, valve 154 can be configured to allow electrosurgical pencil 100 to simply irrigate the surgical site. Accordingly, fluid can only flow out of chamber 144 when handle 142 squeezed (see arrow "B"). More particularly, when handle 142 is squeezed/compressed to a non-expanded condition, fluid "F", contained in chamber 144, is expelled from electrosurgical pencil 100 through valve 154 and fluid passage 146. When handle 142 is allowed to return to its expanded condition, no fluid from the surgical site is drawn into chamber 144 through valve 154.

In another method of use, valve 154 can be configured to allow electrosurgical pencil 100 to simply aspirate the surgical site. In this manner, when handle 142 is squeezed/compressed to its non-expanded condition, air is expelled from chamber 144 through a relief valve 157 (see FIG. 6) when handle 142 is depressed and when handle 142 is allowed to return to its expanded condition fluid from the surgical site is drawn into chamber 144 through valve 154 and fluid passage 146.

It is contemplated that using valve 154 (or multiple valves) enables electrosurgical pencil 100 to be oriented in any direction when performing an aspirating function. However, when performing the irrigating function, in order for fluid "F" to be expelled from chamber 144 upon squeezing/compressing of handle 146, electrosurgical pencil 100 needs to be oriented such that valve 154 is at least partially covered by fluid "F" contained within chamber 144.

It is further envisioned that aspirating/irrigating system 140 can be provided with an additional valve (not shown) which can be used to empty chamber 144 if filled with fluid from the surgical site and/or refill chamber 144 with fluid "F" if emptied. In this manner, if a different type of fluid "F" is desired to be contained in chamber 144 for use during the surgical procedure, chamber 144 can be filled accordingly.

It is further envisioned that aspirating/irrigating system 140 can be removed from housing 102 and replaced with a new aspirating/irrigating system 140. In this manner, when chamber 144 has been filled with fluid from the surgical site or emptied of fluid "F" originally contained therein, used aspirating/irrigating system 140 can be replaced with a new aspirating/irrigating system 140. Moreover, new aspirating/irrigating system 140 can be provided with a different fluid "F" contained therein which different fluid "F" is selected by the surgeon according to the properties desired.

Figures 10, 11:
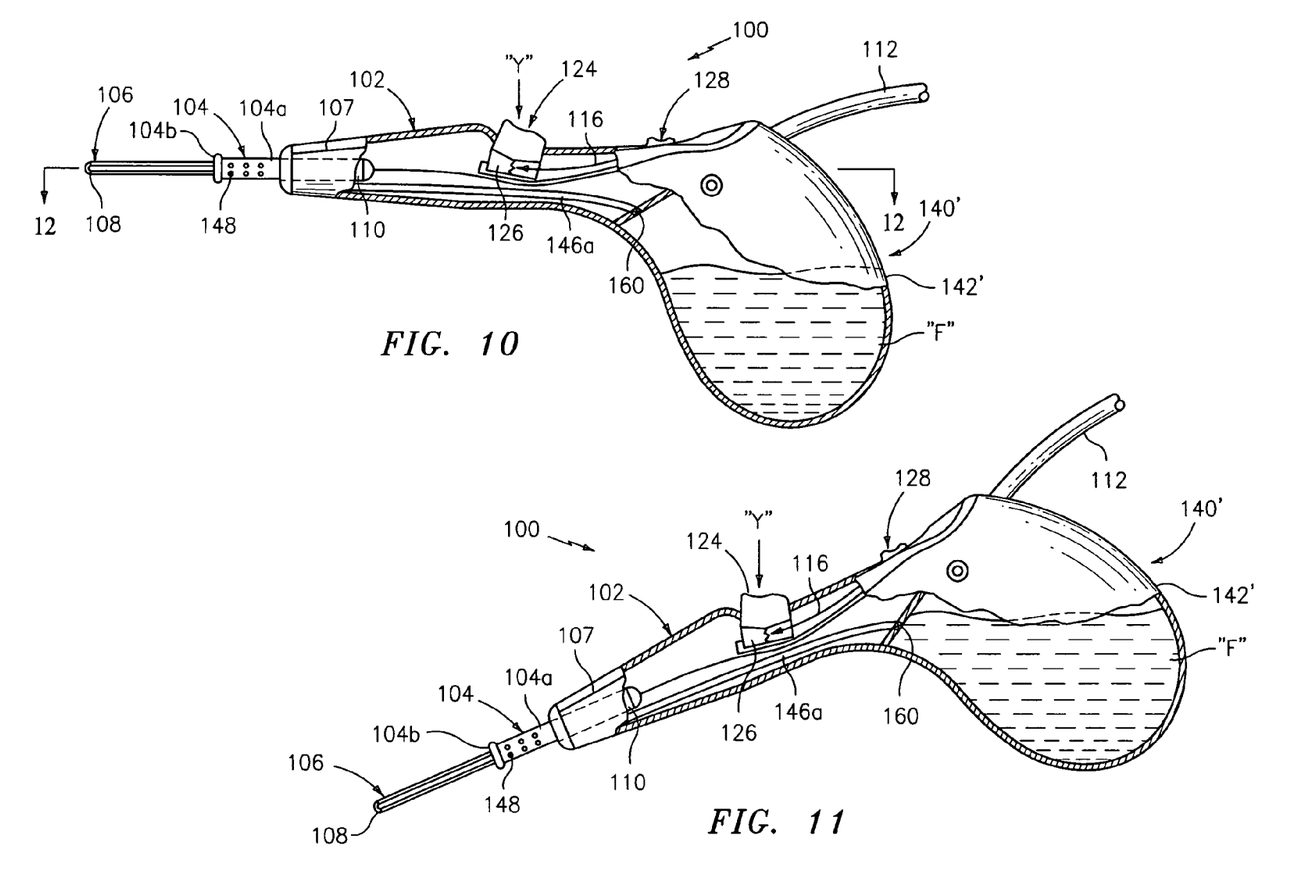
FIG. 10 is a cross-sectional side elevational view of the electrosurgical pencil, according to yet another embodiment of the present disclosure, illustrating a first step in a mode of operation.
FIG. 11 is a cross-sectional side elevational view of the electrosurgical pencil of FIG. 10, illustrating a second step in the mode of operation.
Figure 12:
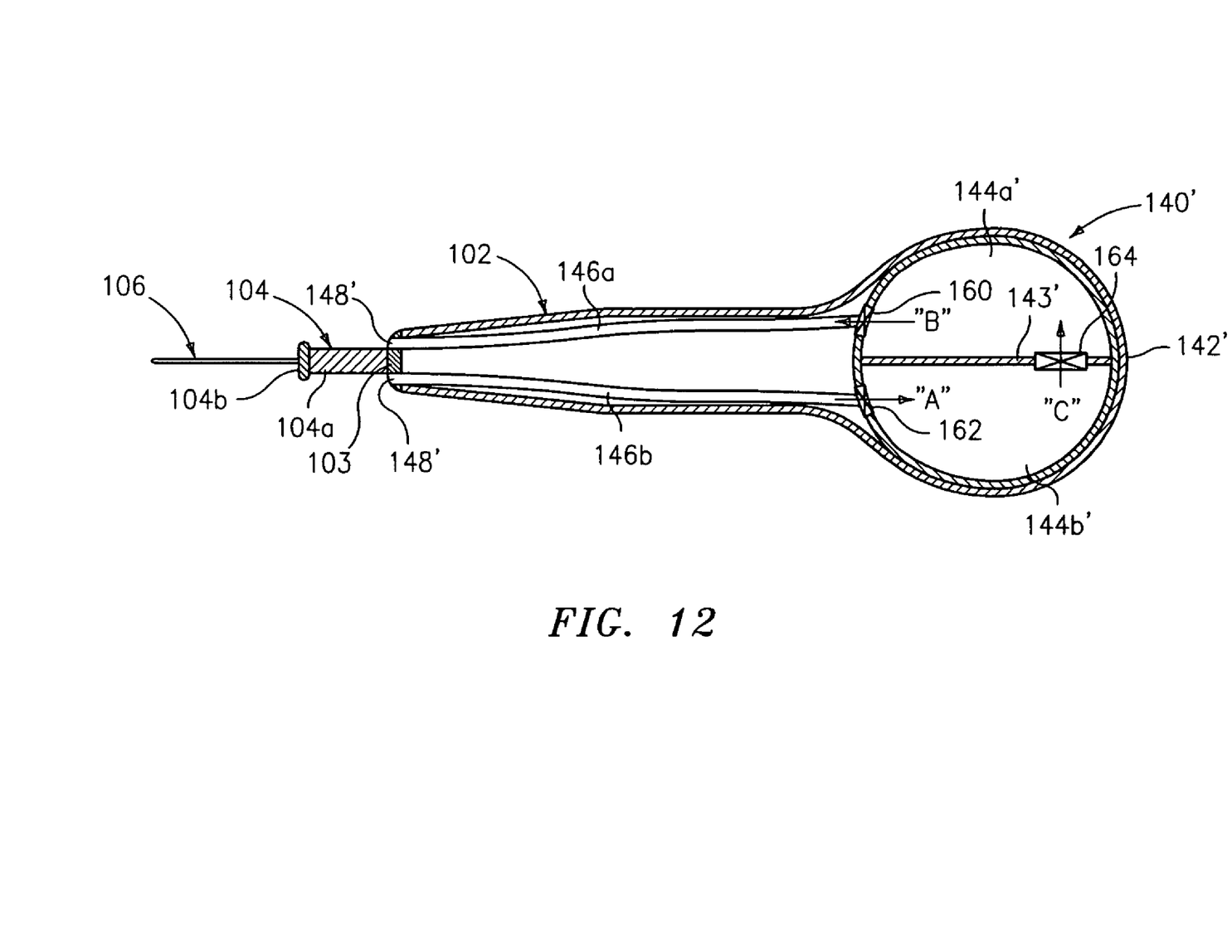
FIG. 12 is a bottom cross-sectional view of the electrosurgical pencil of FIG. 10 taken through X-X of FIG. 10.

Turning now to FIGS. 10-12, in an alternative embodiment, electrosurgical pencil 100 includes an aspirating/irrigating system 140' operatively connected to a proximal end of housing 102. Aspirating/irrigating system 140' includes a resilient handle 142' having a pair of hollow chambers 144a', 144b' (e.g., a fluid collecting chamber and a fluid dispensing chamber) separated by a resilient dividing wall 143'. Aspirating/irrigating system 140' further includes a pair of fluid passages 146a, 146b extending, one each, between chambers 144a', 144b' of handle 142' and respective aperture(s) 148' formed in at least one of a side surface 104a of blade receptacle 104 (see FIGS. 1-3 and 5), a distal surface 104b of blade receptacle 104 (see FIGS. 1 and 4) and distal end 103 of housing 102 (see FIGS. 1 and 4). For the sake of simplicity, aperture(s) 148' are shown formed in distal end 103 of housing 102 only.

As seen in FIGS. 10-12, aspirating/irrigating system 140' further includes a series of valves, preferably three, operatively associated therewith. In one embodiment, a first valve 160 is disposed between fluid passage 146a and chamber 144a', a second valve 162 is disposed between fluid passage 146b and chamber 144b', and an air relief valve 164 is disposed in a dividing wall 143 separating chamber 144a' from chamber 144b'.

In one method of use, first valve 160 is set such that fluid "F" can only flow out of chamber 144a' (as indicated by arrow "B") when handle 142' is squeezed/compressed to its non-expanded condition, while second valve 162 is set such that fluid from the surgical site can only flow into chamber 144b' (as indicated by arrow "A") when handle 142' is allowed to return to its expanded condition. Meanwhile, third valve 164 is set such that fluid (e.g., air) can only flow from chamber 144b' to chamber 144a' (as indicated by arrow "C"). In this manner, when handle 142' is squeezed/compressed to a non-expanded condition, first valve 160 allows fluid "F" to be expelled from electrosurgical instrument 100 through fluid passage 146a, second valve 162 prevents fluid from the surgical site from being expelled from electrosurgical instrument 100 through fluid passage 144b', and relief valve 164 allows passage of air from chamber 144b' to chamber 144a'. Accordingly, the vacuum created within chamber 144a' by the squeezing/compressing of handle 142' is at least partially distributed, preferably equally distributed, between chambers 144a' and 144b' via relief valve 164 (i.e., chambers 144a' and 144b' are in equilibrium or equilibrated). As such, when handle 142' is allowed to return to its expanded condition, relief valve 164 disposed between chambers 144a' and 144b' returns the equilibrium between chambers 144b' and 144a'.

The process is repeated as many times as needed until either chamber 144a' has been emptied of fluid "F" contained therein or until chamber 144b' has been filled with fluid from the surgical site. It is contemplated that each of chambers 144a' and 144b' can be provided with an additional valve (not shown). Preferably, the additional valve for chamber 144a' can be used to refill chamber 144a' with fluid "F" after chamber 144a' has been at least partially emptied during the surgical procedure. The additional valve for chamber 144b' can be used to empty chamber 144b' of fluid from the surgical site after chamber 144b' has been at least partially filled during the surgical procedure.

In an alternative embodiment, it is envisioned that aspirating/irrigating system 140' can be removed from housing 102 and replaced by another or a replacement aspirating/irrigating system 140'. In this manner, when chamber 144a' has been emptied of fluid "F" and/or chamber 144b' has been filled with fluid from the surgical site a new aspirating/irrigating system 140' can be attached to housing 102 as or when needed. Moreover, if a different fluid "F", to be expelled from electrosurgical pencil 100, is desired to be used by the surgeon, a new aspirating/irrigating system 140' containing a different fluid "F" is attached to housing 102 of electrosurgical pencil 100.

Figure 13:
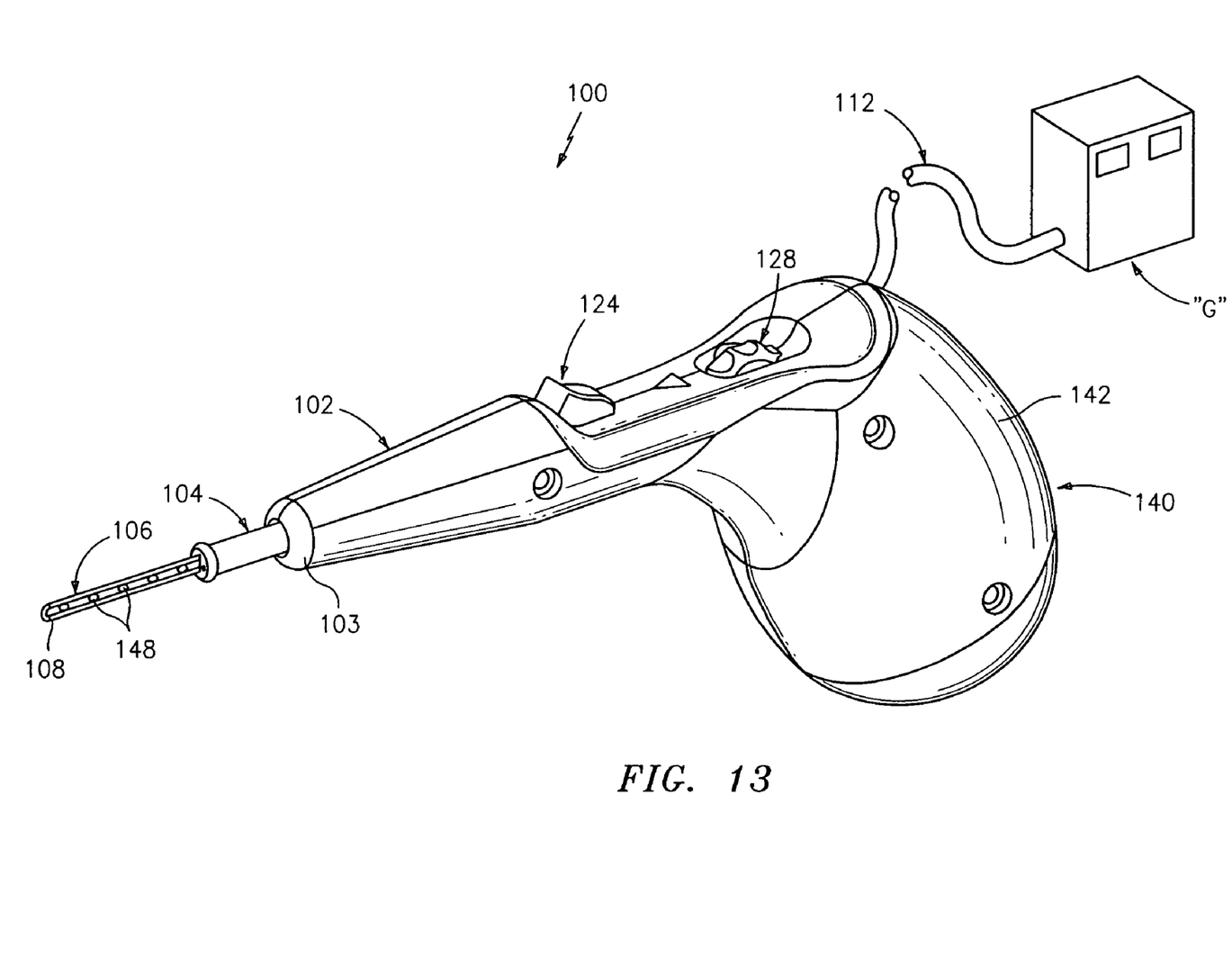
FIG. 13 is a side perspective view of an alternate embodiment according to the present disclosure wherein the aspiration ports are located on an electrode of the electrosurgical pencil.

FIG. 13 shows an alternate embodiment of the present disclosure wherein the fluid dispensing apertures or the aspiration/suction ports 148 are located on the electrode 106 as compared to the apertures shown in FIG. 1 wherein the apertures are located on the blade support 104. FIG. 13 also shows that the fluid dispensing apertures or aspiration/suction ports 148 may also be disposed at the distal-most tip 103 of the distal end of the housing 102.

Although the presently-illustrated embodiments of the preset disclosure show electrosurgical pencils for use with the manual aspirator/irrigator as described herein, it is also contemplated that the manual aspirator/irrigator may be configured for use with other surgical devices, e.g., laparoscopes, coagulators, vessel sealers, ultrasonic devices etc.

It is also envisioned that the presently disclosed aspirator/irrigator may include a hard handle with a compliant pump or bladder disposed therein. A user would successively pump the bladder or pump to dispense or suction fluid to or from the operating site.

While embodiments of electrosurgical pencils according to the present disclosure have been described herein, it is not intended that the disclosure be limited there and that the above description should be construed as merely exemplifications of preferred embodiments. Those skilled in the art will envision other modifications within the scope and spirit of the present disclosure.

The invention claimed is:

1. An electrosurgical pencil, comprising:
   a housing containing a fluid supply source;
   an electrode supported within the housing and extending distally from the housing, the electrode being connected to a source of electrosurgical energy;
   an activation button configured and adapted to selectively supply electrosurgical energy to the electrode upon actuation thereof; and
   an aspirating/irrigating system integrally formed with the housing, wherein the aspirating/irrigating system is configured and adapted to manually perform at least one of delivering a quantity of fluid from the fluid supply source to a target surgical site and withdrawing a quantity of fluid from the target surgical site into the fluid supply source.

2. The electrosurgical pencil according to claim 1, wherein the aspirating/irrigating system includes a resilient handle, the resilient handle defining at least one chamber therein.

3. The electrosurgical pencil according to claim 2, wherein the aspirating/irrigating system further includes at least one fluid passage extending between the at least one chamber of the resilient handle and at least one aperture formed in a distal end of the housing.

4. The electrosurgical pencil according to claim 3, wherein a quantity of fluid is contained within the at least one chamber of the resilient handle.

5. The electrosurgical pencil according to claim 4, wherein the resilient handle has an expanded condition and is compressible to a non-expanded condition, wherein compression of the resilient handle causes the quantity of fluid contained in the at least one chamber of the resilient handle to be urged through the fluid passage and out of the at least one aperture formed in the distal end of the housing.

6. The electrosurgical pencil according to claim 5, wherein when the resilient handle is allowed to return to its expanded condition from the non-expanded condition, fluid is drawn into the at least one chamber of the resilient handle through the fluid passage and in through the at least one aperture formed in the distal end of the housing.

7. The electrosurgical pencil according to claim 6, wherein the aspirating/irrigating system further includes a valve disposed between the at least one fluid passage and the at least one chamber.

8. The electrosurgical pencil according to claim 7, wherein the valve is configured and adapted to allow fluid to pass from the at least one chamber to the at least one fluid passage when the resilient handle is compressed to a non-expanded condition.

9. The electrosurgical pencil according to claim 8, wherein the aspirating/irrigating system further includes a second valve disposed in fluid communication with a second chamber.

10. The electrosurgical pencil according to claim 9, wherein the second valve is configured and adapted to allow fluid to pass into the second chamber when the resilient handle is allowed to return to its expanded condition.

11. The electrosurgical pencil according to claim 10, further including a mode selector supported on the housing, the mode selector being electrically connected to the source of electrosurgical energy and is configured and adapted to vary a waveform duty cycle which is delivered from the source of electrosurgical energy to the electrode.

12. The electrosurgical pencil according to claim 11, wherein the mode selector is configured and adapted to vary the waveform duty cycle to produce at least one of a cutting, blending and coagulating effect.

13. The electrosurgical pencil according to claim 8, wherein the second valve is disposed between a second chamber in the handle and a second fluid passage which communicates with at least one aperture at the distal end of the housing.

14. The electrosurgical pencil according to claim 2, wherein the resilient handle is fabricated from rubber.

15. The electrosurgical pencil according to claim 1, wherein the resilient handle of the aspirating/irrigating system defines first and second chambers separated by a dividing member, and first and second fluid passages extending respectively between the first and second chambers of the resilient handle and the at least one aperture formed in a distal end of the housing.

16. The electrosurgical pencil according to claim 15, wherein the resilient handle has an expanded condition and is compressible to a non-expanded condition.

17. The electrosurgical pencil according to claim 16, wherein the aspirating/irrigating system includes:
   a first valve disposed between the first fluid passage and the first chamber;
   a second valve disposed between the second fluid passage and the second chamber; and
   a relief valve for equalizing the environmental conditions between the first and second chambers.

18. The electrosurgical pencil according to claim 17, wherein the first chamber includes a quantity of fluid contained therein.

19. The electrosurgical pencil according to claim 18, wherein the first valve is configured and adapted to allow the quantity of fluid contained in the first chamber to pass from the first chamber to the first fluid passage when the handle is compressed to a non-expanded condition.

20. The electrosurgical pencil according to claim 19, wherein the second valve is configured and adapted to allow fluid to be drawn into the second chamber when the handle is allowed to return to the expanded condition from the non-expanded condition.

21. An electrosurgical pencil for selectively providing electrosurgical energy from a source of electrosurgical energy to tissue, the electrosurgical pencil having an electrode electrically connected to the source of electrosurgical energy, the electrosurgical pencil comprising:
a housing containing a fluid supply source, the housing configured and adapted to receive the electrode in a distal end thereof; and
a manual aspirating/irrigating system supported on the housing, the aspirating/irrigating system including:
a body portion defining at least one chamber therein for containing the fluid supply source and
a fluid passage extending between an aperture formed in a distal end of the housing and the at least one chamber, wherein the body portion has an expanded condition in which the at least one chamber has a first volume and a non-expanded condition in which the at least one chamber has a second volume which is less than the first volume.

22. The electrosurgical pencil according to claim 21, wherein aspirating/irrigating system includes a first valve disposed between the at least one chamber and the fluid passage.

23. The electrosurgical pencil according to claim 22, wherein the aspirating/irrigating system includes a second valve disposed in the body portion and in fluid communication with the at least one chamber.

24. The electrosurgical pencil according to claim 23, wherein the first valve is configured and adapted to allow fluid to pass out of the at least one chamber and the second valve is configured and adapted to allow fluid to enter the at least one chamber.

25. The electrosurgical pencil according to claim 24, wherein the at least one chamber of the body portion contains a quantity of fluid.

26. The electrosurgical pencil according to claim 25, wherein when the body portion is compressed from the first volume to the second volume the quantity of fluid is urged out of one of the chambers through the first valve and when the body portion is allowed to return to the first volume from the second volume fluid enters a different one of the chambers from the second valve.

27. A method of aspirating/irrigating a target surgical site during an electrosurgical procedure, comprising the steps of:
providing an electrosurgical pencil comprising:
a housing containing a fluid Supply source therein;
an electrode supported within the housing and extending distally from the housing, the electrode being connected to a source of electrosurgical energy;
an activation button supported on the housing, the activation button being configured and adapted to complete a control loop extending from the source of electrosurgical energy upon actuation thereof; and
an aspirating/irrigating system operatively connected to the housing, wherein the aspirating/irrigating system includes a resilient handle which is configured and adapted to deliver a quantity of fluid from the fluid supply source contained in the handle to a target surgical site when the handle is compressed and withdraw a quantity of fluid into the fluid supply source from the target surgical site when the handle is allowed to expand;
performing an electrocautery function at a target surgical site; and
at least one of compressing the handle to deliver the quantity of fluid contained in the fluid supply source of the handle to the target surgical site and allowing the handle to expand to withdraw a quantity of fluid from the target surgical site into the fluid supply source of the handle.

28. The method according to claim 27, wherein the aspirating/irrigating system includes a fluid passage extending between an aperture formed in a distal end of the housing and the fluid supply source.

29. The method according to claim 28, further including the steps of:
partially compressing the handle and placing the aperture in a quantity of fluid and allowing the handle to expand to withdraw fluid into the fluid supply source.

30. An electrosurgical pencil, comprising:
a housing containing a fluid supply source therein;
an electrode supported within the housing and extending distally from the housing, the electrode being connected to a source of electrosurgical energy;
an activation button configured and adapted to selectively supply electrosurgical energy to the electrode upon actuation thereof; and
an aspirating/irrigating system supported on the housing, wherein the aspirating/irrigating system is configured and adapted to manually perform at least one of delivering a quantity of fluid to a target surgical site and withdrawing a quantity of fluid from the target surgical site; said aspirating/irrigating system including:
a resilient handle which defines at least one chamber therein for containing the fluid supply source, wherein said resilient handle is configured such that compression of said handle causes the delivery of a quantity of fluid from the fluid supply source to a target surgical site and expansion of said handle to an uncompressed condition causes the withdrawal of a quantity of fluid from a target surgical site to the fluid supply source; and
a fluid passage extending between the at least one chamber of the resilient handle and at least one aperture formed in a distal end of the housing; said at least one aperture being disposed about the periphery of the distal end of the housing.

31. An electrosurgical pencil according to claim 30 wherein said at least one aperture is disposed at the distal-most tip of the distal end of the housing.

32. An electrosurgical pencil according to claim 30 wherein said at least one aperture is disposed in the electrode.

* * * * *